United States Patent
Bak et al.

(10) Patent No.: US 7,851,683 B2
(45) Date of Patent: Dec. 14, 2010

(54) *GUZMANIA* HYBRID NAMED 'ROCK'

(75) Inventors: Elly Bak, Rijsenhout (NL); Nicolaas D. M. Steur, Oude Niedorp (NL)

(73) Assignee: Corn. Bak B.V., Assendelft (NL)

( * ) Notice: Subject to any disclaimer, the term of this patent is extended or adjusted under 35 U.S.C. 154(b) by 354 days.

(21) Appl. No.: 12/007,419

(22) Filed: Jan. 10, 2008

(65) Prior Publication Data
US 2009/0183271 A1    Jul. 16, 2009

(51) Int. Cl.
*A01H 5/00* (2006.01)

(52) U.S. Cl. .................... 800/323; 800/260; Plt./371

(58) Field of Classification Search .................... None
See application file for complete search history.

(56) References Cited

U.S. PATENT DOCUMENTS

PP12,769 P2 *  7/2002  Bak et al. .................... Plt./371
PP13,041 P2 * 10/2002  Kent .......................... Plt./371

* cited by examiner

*Primary Examiner*—David H Kruse
(74) *Attorney, Agent, or Firm*—Foley & Lardner LLP

(57) ABSTRACT

A new and distinct *Guzmania* hybrid named 'ROCK' characterized by solid growth habit; funnel-form rosette plant, measuring about 42 cm in height (above the pot when flowering); numerous, relatively narrow, green color foliage, measuring about 30 cm in length and about 2.7 cm to 3.7 cm in width; superior floral bract production; bracts have a unique gray-purple color which distinguishes this cultivar from typical *Guzmania*; compound inflorescence, measuring about 38 to 48 cm in height and about 50 cm in diameter; and long-lasting habit.

4 Claims, 2 Drawing Sheets
(2 of 2 Drawing Sheet(s) Filed in Color)

GUZMANIA HYBRID NAMED 'ROCK'

FIELD OF THE INVENTION

The present invention relates to a new, distinct and stable hybrid of *Guzmania* hybrid, hereinafter referred to as 'ROCK'. The present invention relates to seeds which are the *Guzmania* hybrid 'ROCK', as well as, plants and plant parts produced by these seeds which have all of the morphological and physiological characteristics of the *Guzmania* hybrid 'ROCK'. The present invention also relates to methods for producing these seeds and plants of the *Guzmania* hybrid 'ROCK'. Furthermore, the present invention relates to a method of producing progeny *Guzmania* plants by crossing *Guzmania* 'ROCK', as either the female or seed or male or pollen parent, with another *Guzmania* plant and selecting progeny.

BACKGROUND OF THE INVENTION

The present invention relates to a new, distinct and stable hybrid of *Guzmania* hybrid, hereinafter referred to by the variety denomination 'ROCK'. The new *Guzmania* 'ROCK' originated from a cross made in a controlled breeding program by the inventors in 2002, and then first flowered in 2005, in Assendelft, The Netherlands. The female or seed parent is the *Guzmania wittmackii* inbred line identified by code 0232493002 (unpatented) The male or pollen parent is the *Guzmania lingulata* minor inbred line identified by code 02324011 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'ROCK' was developed through a controlled breeding program and exhibits unique, desirable and stable characteristics.

SUMMARY OF THE INVENTION

The present invention provides *Guzmania* plant selections that are solid, small-sized, long-lasting hybrids with superior bract production and gray-purple inflorescence that exhibits good keeping quality. The present invention also provides *Guzmania* plant selections with a round, spike-like inflorescence with a unique orange color which distinguishes the new cultivar from typical *Guzmania*.

These and other objectives have been achieved in accordance with the present invention which provides 'ROCK' as a new *Guzmania* cultivar that is a product of a planned breeding program conducted by the inventors, Elly Bak and Nico D. M. Steur, in Assendelft, The Netherlands, in 2002. The female or seed parent is the *Guzmania wittmackii* inbred line identified by the code 0232493002 (unpatented). The male or pollen parent is the *Guzmania lingulata* minor inbred line identified by the code 02324011 (unpatented).

Both parental cultivars have a sufficient degree of homozygosity such that the progeny of the cross are genotypically and phenotypically uniform. The cultivar 'ROCK' therefore can be produced by sexual reproduction by crossing the parental inbred lines identified by the codes 0232493002 and 02324011 to produce a population of progeny plants, each of which has the combination of characteristics as herein disclosed for the new cultivar 'ROCK'.

Seeds which are cultivar 'ROCK' are produced by crossing the parental inbred lines identified by the codes 0232493002 and 02324011, and are deposited with the American Type Culture Collection, 10801 University Boulevard, Manassas, Va. 20110-2209 (ATCC Patent Deposit Designation No. PTA-8741). 2500 seeds were deposited with the ATCC on Oct. 30, 2007.

OBJECTS OF THE INVENTION

The present invention relates to seeds which produce *Guzmania* cultivar 'ROCK'. The present invention also relates to *Guzmania* plants, and parts thereof, having all the physiological and morphological characteristics of *Guzmania* cultivar 'ROCK'. The present invention relates to a plant produced from seeds which are *Guzmania* cultivar 'ROCK'. The present invention also relates to plant parts, such as pollen, seeds or inflorescence produced by *Guzmania* cultivar 'ROCK'.

The present invention relates to method of producing seed which are *Guzmania* cultivar 'ROCK', by crossing *Guzmania wittmackii* inbred line identified by code 0232493002 (unpatented) as the female or seed parent with *Guzmania lingulata* minor inbred line identified by code 02324011 (unpatented) as the male or pollen parent, and the reciprocate cross with 02324011 as the male parent and 0232493002 as the female parent, and harvesting seeds produced from said crosses.

The present invention also relates to a method of producing plants having all the physiological and morphological characteristics of the *Guzmania* cultivar 'ROCK' comprising the steps of (a) crossing *Guzmania wittmackii* inbred line identified by code 0232493002 (unpatented) as the female or seed parent with *Guzmania lingulata* minor inbred line identified by code 02324011 (unpatented) as the male or pollen parent; (b) harvesting seeds produced from said cross; and (c) producing plants from said harvested seeds.

The present invention also relates to producing progeny plants from the cross of *Guzmania* cultivar 'ROCK', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* cultivar 'ROCK' showing the colors as true as is reasonably possible with colored reproductions of this type. Colors in the photographs may differ slightly from the color values cited in the detailed botanical description which accurately describes the color of 'ROCK'.

DETAILED BOTANICAL DESCRIPTION

Figure 1:
FIG. 1 shows a side view perspective of the primary and top bracts produced by a typical potted, flowering plant of 'ROCK', at 11 months of age from potting size.
Figure 2:
FIG. 2 shows a close-up top view perspective of the inflorescence and top bracts produced by a typical potted, flowering plant of 'ROCK', at 11 months of age from potting size.

The present invention was created by the inventors, Elly Bak and Nicolaas D. M. Steur in 2002, and flowered for the first time in 2005 in Assendeltt, The Netherlands.

This invention is directed to *Guzmania* plant having all the morphological and physiological characteristics of the cultivar 'ROCK' produced from seeds which are the product of the cross of the *Guzmania wittmackii* inbred line identified by code 0232493002 (unpatented) as the female or seed parent with the *Guzmania lingulata* minor inbred line identified by code 02324011 (unpatented) as the male or pollen parent. Both parents have a sufficient degree of homozygosity such that the progeny of the cross were, and continue to be, phenotypically uniform. The new cultivar 'ROCK' can therefore be produced by sexual reproduction by crossing of the inbred selections identified by the codes 0232493002 and 02324011 to produce a population of progeny plants, each of which has the combination of characteristics herein disclosed for the new cultivar 'ROCK'.

The new cultivar 'ROCK' can also be produced by asexually reproducing progeny from the cross of the *Guzmania* inbred lines identified by the codes 0232493002 and 02324011. Asexual reproduction of the new cultivar by cuttings was first performed in 2005, in Assendelft, The Netherlands. The first 'ROCK' plants propagated through the use of cuttings flowered in 2006, in Assendelft, The Netherlands, and have demonstrated that the new cultivar reproduces true-to-type and that the combination of characteristics as herein disclosed for the new cultivar are firmly fixed and retain through successive generations of asexual reproduction.

BRIEF DESCRIPTION OF THE INVENTION

The following traits have been repeatedly observed and are determined to be unique characteristics of 'ROCK' which in combination distinguish this *Guzmania* as a new and distinct cultivar:

1. Solid growth habit;
2. Funnel-form rosette plant, measuring about 42 cm in height (above the pot when flowering);
3. Numerous, relatively narrow, green color foliage, measuring about 30 cm in length and about 2.7 cm to 3.7 cm in width;
4. Superior floral bract production;
5. Bracts have a unique gray-purple color which distinguishes this cultivar from typical *Guzmania;*
6. Compound inflorescence, measuring about 38 to 48 cm in height and about 50 cm in diameter; and
7. Long-lasting habit.

Of the many commercial cultivars known to the present inventors, the most similar in comparison to the new *Guzmania* cultivar 'ROCK' is the *Guzmania* cultivar 'JAZZ' (granted, U.S. Pat. No. 6,365,801 and Plant Patent No. 12,769). Plants of the new cultivar 'ROCK' differ from plants of 'JAZZ' primarily in inflorescence color. Plants of 'ROCK' produce inflorescence which are gray-purple in color with white tips whereas plants of 'JAZZ' produce inflorescence which are orange-red in color.

'ROCK' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by acetylene treatment. Since treatment with acetylene to induce flowering disrupts normal watering and fertilization regimens, acetylene treatment of relatively smaller plants adversely affects the growth of the plant.

The aforementioned photographs, together with the following observations, measurements and values describe the new *Guzmania* 'ROCK' as grown in a greenhouse in Assendelft, The Netherlands, under conditions which closely approximate those generally used in commercial practice. Plants of 'ROCK' were grown in a greenhouse with day temperatures ranging from 20° C. to 28° C. and night temperatures ranging from 18° C. to 23° C. No artificial lighting or photoperiodic treatments were conducted, but plants of 'ROCK' are forced into flowering by adding acetylene. The following fertilizer is added when growing plants of 'ROCK': 1 part nitrogen, 0.6 parts phosphor, 2 parts Kalium and 0.1 parts magnesium.

Color references are made to the Royal Horticultural Society Colour Chart (RHS), unknown edition, except where general colors of ordinary significance are used. Color values were taken under daylight conditions in a greenhouse in Assendelft, The Netherlands. The age of the plants of 'ROCK' described is about 10 weeks after treatment with acetylene.

Classification:

Botanical: *Guzmania* sp.

Parentage:
Female Parent: *Guzmania wittmackii* inbred line identified by code 0232493002 (unpatented)
Male Parent: *Guzmania lingulata* minor inbred line identified by code 02324011 (unpatented)
Plant:
General Appearance and Form:
   Height: About 38 cm to 48 cm (when flowering)
   Width: About 50 cm
   Shape: Funnel form rosette
Growth habit: Stemless
Plant Vigor: Good
Flowering Season: A fully grown plant can flower year round, starting 12 to 14 weeks after induction of natural light or trough treatment with acetylene.
Cold Tolerance: Frost tender. Temperatures below 5° C. may damage plants.
Fragrance: None
Foliage:
Quantity: About 16 to 22 (depending on the size of the plant)
Size of Leaf:
   Length: About 20 cm to 40 cm
   Width: About 2.7 cm to 3.7 cm
Overall Shape: Linear-lanceolate
Apex Shape: Acute
Base Shape: Strap-like around central axis
Margin: Entire
Texture: Smooth
Orientation: Leaf blades arch continuously from base.
Color: Leaf color can vary somewhat depending on growing conditions and application of fertilizer. Typically, RHS 137 B; however, if less fertilizer is applied, color ranges can be between RHS 137B and RHS 144A.
   Upper and Under Surfaces:
      Mature leaf: Green, RHS 137B
      Immature leaf: Green, RHS 137B
Venation: None
Inflorescence:
Borne: Erect stalks
Shape: Compound
Size:
   Length: About 12 cm
   Diameter: About 15 cm
Time of Bloom: A fully grown plant can produce an inflorescence containing about 80 flowers divided over about 9 branches (depending on the size of the plant), and can bloom the whole year starting about twelve (12) to fourteen (14) weeks after natural induction or through treatment with acetylene.
Duration of Bloom: Each flower blooms one (1) day and the total blooming of the whole inflorescence is about five (5) weeks.
Petals:
   Number: 3 per flower
   Length: About 5.5 cm
   Width: About 0.7 cm
   Overall Shape: Ligulate
   Apex Shape: Cuspidate
   Base Shape: Fused
   Color:
      Upper surface: Yellow, RHS 7B,
      Lower surface: Yellow, RHS 7B
Sepals:
   Number: 3 per flower
   Length: About 2.5 cm
   Width: About 0.5 cm
   Overall Shape: Ligulate
   Apex Shape: Acute
   Base Shape: Fused
   Color: Membranous white
Bracts:
Scape Bracts:
   Quantity: About 7
   Arrangement: Alternate
   Size:
      Length: About 24 cm (lowest) to about 13 cm (scape bracts positioned just below the primary bracts).
      Width: About 3.2 cm
   Overall shape: Recurved and oval lanceolate
   Apex shape: Acute
   Base shape: Fused
   Margin: Entire
   Texture: Smooth
   Color: (Apex/Scape/Middle) Scape part is a small part the middle part, which is small at the lowest scape bracts and becomes a big part at the scape bracts just below the primary bracts.
      Upper surface: (Apex: Green, RHS 137B/Scape: Yellow-green, RHS 144B/Middle: Greyed-purple, RHS 187C)
      Under surface: (Apex: Green, RHS 137C/Scape: Yellow-green, RHS 144B/Middle: Greyed-purple, RHS 187C
Primary Bracts:
   Quantity: About 12
   Arrangement: Alternate
   Size:
      Length: About 12 cm (lowest) to about 7 cm (primary bracts become shorter closer to the top of plant)
      Width: About 3.4 cm
   Overall shape: Recurved and oval lanceolate
   Apex shape: Acute
   Base shape: Fused
   Margin: Entire
   Texture: Smooth
   Color:
      Upper surface: Primarily grey-purple, RHS 187C with white, RHS 158C, at the apex
      Under surface: Greyed-purple, RHS 187C
Floral bracts: Disposed within the inflorescence.
Reproductive Organs:
Androecium:
   Stamen:
      Number: 6 per flower
      Length: About 4 cm
      Diameter: About 0.1 cm
      Color: Yellow-white, RHS 158C
   Anther:
      Length: About 0.5 cm
      Color: Yellow-white, RHS 158A
   Pollen:
      Amount: Scarce
      Color: Yellow-white, RHS 158A
Gynoecium:
   Pistil:
      Number: 1 per flower
      Length: About 4.5 cm
   Stigma:
      Shape: 3-parted
      Width: About 0.2 cm
      Color: Yellow-white, RHS 158A Style:
  Length: About 4.5 cm
  Color: Greyed-yellow, RHS 160A
Ovary:
  Position: Superior
  Shape: Conical
  Length: About 1 cm
  Diameter: About 0.3 cm
  Color: Green, RHS 142C
SEEDS/FRUIT: Sterile hybrid, therefore, no seed or fruit produced.
DISEASE/PEST RESISTANCE: No observations made.
DISEASE/PEST SUSCEPTIBILITY: No observations made.

We claim:

1. A *Guzmania* plant named 'ROCK', representative seed having been deposited with the American Type Culture Collection (ATCC) and accorded Patent Deposit Designation No.: PTA-8741.

2. *Guzmania* seed having American Type Culture Collection (ATCC) Patent Deposit Designation No.: PTA-8741.

3. A plant part obtained from the *Guzmania* plant of claim 1.

4. A method of producing *Guzmania* progeny plant comprising the steps of (a) crossing *Guzmania* 'ROCK' produced from seed accorded American Type Culture Collection (ATCC) Patent Deposit Designation No.: PTA-8741 as a female parent with another *Guzmania* plant, and (b) selecting progeny.

* * * * *